US007713922B2

(12) United States Patent
Duprey et al.

(10) Patent No.: US 7,713,922 B2

(45) Date of Patent: May 11, 2010

(54) PERFUME COMPOSITIONS

(75) Inventors: Roger John Henry Duprey, Kent (GB); Keith Douglas Perring, Kent (GB); Jeremy Nicholas Ness, Kent (GB)

(73) Assignee: Quest International Services B.V., Naarden (NL)

( * ) Notice: Subject to any disclaimer, the term of this patent is extended or adjusted under 35 U.S.C. 154(b) by 0 days.

(21) Appl. No.: 11/992,420

(22) PCT Filed: Sep. 22, 2006

(86) PCT No.: PCT/GB2006/003506

§ 371 (c)(1),
(2), (4) Date: Mar. 21, 2008

(87) PCT Pub. No.: WO2007/034187

PCT Pub. Date: Mar. 29, 2007

(65) Prior Publication Data

US 2009/0137450 A1 May 28, 2009

(30) Foreign Application Priority Data

Sep. 23, 2005 (GB) ................................ 0519437.8

(51) Int. Cl.
*A61K 8/00* (2006.01)
*A61K 8/18* (2006.01)
*A61Q 13/00* (2006.01)

(52) U.S. Cl. .............................. 512/1; 512/20; 512/25; 512/26; 512/27

(58) Field of Classification Search ..................... 512/1, 512/20, 25, 26, 27; 252/522; 568/300
See application file for complete search history.

(56) References Cited

U.S. PATENT DOCUMENTS 3,461,085 A * 8/1969 Toet et al. ..................... 512/20
3,548,006 A * 12/1970 Scriabine .................... 568/425
3,576,760 A 4/1971 Gould et al. ................ 252/403
4,145,184 A 3/1979 Brain et al. ..................... 8/137
4,209,417 A 6/1980 Whyte ................... 252/174.11
4,339,356 A 7/1982 Whyte ........................ 252/522
4,383,943 A 5/1983 Britten-Kelly et al. ...... 522/522
5,066,640 A 11/1991 Voss et al. ..................... 512/21
5,137,646 A 8/1992 Schmidt et al. .............. 252/8.8
5,154,842 A 10/1992 Walley et al. ................ 252/8.6
2004/0097397 A1* 5/2004 Mohr et al. .................... 512/1

FOREIGN PATENT DOCUMENTS

EP 1 329 497 A2 7/2003
FR 1489241 * 6/1967
FR 1.489.241 7/1967
WO WO 2004/016234 A1 2/2004

* cited by examiner

*Primary Examiner*—James Seidleck
*Assistant Examiner*—Aaron Greso
(74) *Attorney, Agent, or Firm*—Morgan Lewis & Bockius LLP

(57) ABSTRACT

Perfume compositions comprise over 50% by weight of perfume ingredients characterized by possessing (i) a molecular formula possessing from 8 to 13 carbon atoms, including at least one phenyl moiety, substituted or unsubstituted; (ii) an octanol/water partition coefficient (log P) of at least 1.5; (iii) a saturated vapour pressure (SVP) of at least 3 micron Hg at 25 C; and (iv) belonging to one of the following groups (i) ethers of general formula R1OR2; (ii) aldehydes or nitriles of general formula RIX, wherein X is CHO (formyl group) or CN (cyano group); (iii) esters of general formula R1CO2R2; (iv) alcohols or phenols of general formula R1OH; or (v) ketones of general formula R1COR2; wherein R1 and R2 are alkyl, aryl, aralkyl or alkaryl residues, optionally substituted, whose alkyl moieties may be straight-chained or branched, and which may be linked as part of a ring structure. The compositions find particular application in the form of encapsulates for use in consumer products.

11 Claims, No Drawings

PERFUME COMPOSITIONS

FIELD OF THE INVENTION

This invention relates to perfume compositions (also referred to as fragrance compositions). The invention relates particularly, but not exclusively, to compositions comprising non-substantive materials where such compositions can behave in a substantive manner (referred to herein as performant compositions).

BACKGROUND OF THE INVENTION

It is common to add fragrance compositions to consumer products to deliver a fresh (or clean) odour to targeted substrates (such as textiles, hard surfaces, skin, hair etc.) and to provide an olfactory aesthetic benefit.

Efforts continue to be made to find improvements in the performance of fragrance compositions, including their in-product shelf life, their delivery effectiveness and their longevity or substantivity on various substrates.

For example, during cleaning processes a substantial amount of fragrance is lost with rinse water and through drying, and it is extremely important to be able to overcome these process conditions and ensure that the fragrance material left on the substrate provides maximum fragrance effect via the minimum amount of material, i.e. there is a need to be able to create highly substantive fragrance materials.

Substantive fragrance ingredients (also known as "enduring perfumes") are those that effectively deposit onto a substrate in, for example, a cleaning process and are detectable (olfactively) on the wet and subsequently dried substrate. Persons skilled in the art of creating fragrance compositions, usually have some knowledge of particular fragrance ingredients that are substantive (in general, such ingredients are heavy, insoluble and non-volatile).

Fragrance performance may also be enhanced through the use of encapsulation systems to protect and release them in a controlled manner.

Encapsulation systems are usually designed to achieve two objectives.

The first objective relates to the protection of ingredients entrapped in such systems. The second objective is to control, depending on the final application, the release of the entrapped ingredient. In particular, if the entrapped ingredient is volatile, it is important to prevent its release during storage, but at the same time ensuring release of the entrapped volatile ingredient during use. Release is normally triggered by conditions that are typical of such use (e.g. heat, moisture).

An example of such encapsulation technology is embodied in microcapsules filled with perfume, which are commercially marketed by, e.g., Reed Pacific (in Australia), Celessence (in the UK), Hallcrest Inc. (in the US), or Euracli (in France). These microcapsules are adapted to break under friction and provide an instant "burst" of the fragrance when the microcapsules are ruptured. Microcapsules of the aminoplast type are used in the textile industry and include microcapsules that are deposited on the fabric surface during the fabric finishing operation. These microcapsules are generally removed in the course of subsequent domestic washing, but typically can withstand about five washes before the fabric or skin beneficiating ingredients lose their intended effect.

The preparation of microcapsules for encapsulation technology is a known art; preparation methods are, for instance, described in detail in a handbook edited by Simon Benita ("Microencapsulation; Methods and Industrial Applications, Marcel Dekker, Inc. N.Y., 1996), the contents of which are incorporated herein by reference for the preparation techniques described therein.

Further reference is made to a number of patent publications that describe the use of encapsulated fragrance in household applications, such as detergent compositions and in fabric softener products. For example, U.S. Pat. No. 4,145,184 describes detergent compositions that contain perfumes in the form of friable microcapsules. Preferred materials for the microcapsule shell walls are the aminoplast polymers comprising the reaction product of urea and aldehyde.

U.S. Pat. No. 5,137,646 describes the preparation and use of perfumed particles, which are stable in fluid compositions and which are designed to break and release the perfume as the particle is used. This patent describes fabric softener compositions comprising perfume particles comprising perfume dispersed in a solid core comprising a water-insoluble polymeric carrier material. These cores are encapsulated by a friable coating, such coating being preferably an aminoplast polymer.

Encapsulated fragrance composition particles may be mixed into, for example, laundry compositions. Perfume may be combined with water-soluble polymer(s) to form particles that are then added to a laundry composition, as described in U.S. Pat. Nos. 4,209,417; 4,339,356; 3,576,760; and 5,154,842.

SUMMARY OF THE INVENTION

A perfume composition of this invention comprises over 50% by weight of perfume ingredients that are characterized by (i) a molecular formula possessing from 8 to 13 carbon atoms, including at least one phenyl moiety, substituted or unsubstituted; (ii) an octanol/water partition coefficient (logP) of at least 1.5; (iii) a saturated vapour pressure (SVP) of at least 3 micron Hg at 25° C.; and (iv) membership of one of the following groups:

1) ethers of general formula $R_1OR_2$;
2) aldehydes or nitrites of general formula $R_1$,X, wherein X is CHO (formyl group) or CN (cyano group);
3) esters of general formula $R_1CO_2R_2$;
4) alcohols or phenols of general formula $R_1OH$; or
5) ketones of general formula $R_1COR_2$ wherein $R_1$ and $R_2$ are alkyl, aryl, aralkyl or alkaryl residues, optionally substituted, whose alkyl moieties may be straight-chained or branched, and which may be linked as part of a ring structure;

provided that (a) essential oils are excluded as components of the invention; (b) where a perfume ingredient could be assigned to more than one of the above groups, said ingredient is allocated to the group having the lower or lowest number; (c) perfume ingredients used as non-odorous or very low odour solvents or vehicles are not included in the calculation of the percentage composition; and (d) at least three of the groups (1) to (5) must each comprise materials amounting to at least 5% by weight of the perfume composition.

Any balance of the perfume composition to make up 100% can be selected from known fragrance materials and will generally be chosen to produce a composition with desired odour characteristics. If the balance of materials includes any essential oils, then any component ingredients of those essential oils falling in groups 1 to 5 are to be excluded from the calculation of amounts of ingredients in groups 1 to 5 in accordance with the invention. Any diluents, solvents or other odourless or very low odour materials included in the composition are excluded when calculating the percentage of perfume ingredients falling in groups 1 to 5, with these percentages being based on the total amount of odiferous fragrance materials present in the composition.

The perfume ingredients and any additional fragrance materials can be selected from a wide range of fragrance materials which are well known to those skilled in the art and which include, inter alia, alcohols, ketones, aldehydes, esters, ethers, nitrites, and alkenes such as terpenes. A listing of common fragrance materials can be found in various reference sources, for example, "Perfume and Flavor Chemicals", Vols. I and II; Steffen Arctander Allured Pub. Co. (1994) and "Perfumes: Art, Science and Technology"; Muller, P. M. and Lamparsky, D., Blaclde Academic and Professional (1994).

Preferably the perfume composition includes perfume ingredients falling in at least four, preferably all five, of the groups.

Preferably at least one group, more preferably at least two groups, includes perfume ingredients amounting to at least 10% of the weight of the perfume composition.

Desirably at least one group, possibly at least two groups or more, includes at least two, preferably at least three, different perfume ingredients.

Preferably, perfume compositions of the present invention comprise at least 60% by weight of perfume ingredients falling in groups 1 to 5; more preferably at least 70% by weight; even more preferably at least 80% by weight.

Preferably, at least one, possibly all, of the perfume ingredients falling in groups 1 to 5 has an SVP of at least 25 micron Hg at 25° C.; more preferably at least 125 micron Hg at 25° C.

Preferably, the perfume compositions of the present invention are encapsulated.

The term encapsulation as used herein generally refers to the retention of a composition or area within a compartment, delineated by a physical barrier. For example, the encapsulated fragrance compositions described herein, refer to fragrance materials that are retained within, and surrounded by a physical barrier. Thus, included within the term "encapsulation," are compositions that are coated, insofar as the coating provides a physical barrier. The term "microcapsule" as used herein, refers to an encapsulated composition, wherein the composition exists as encapsulated capsules or beads (matrix capsules) ranging in diameter from 1 μm to 2 mm, preferably for shell capsules from 1 μm to 100 μm, even more preferably from 1 μm to 50 μm, and even more preferably still from 2 μm to 10 μm, and preferably for beads from 20 μm to 150 μm, and even more preferably from 30 μm to 100 μm.

Typical non-limiting types of microcapsules include shear release capsules (such as aminoplasts, coacervates, polycondensates, capsules made by interfacial polymerization); matrix capsules (such as beads); and water-soluble capsules (such as spray-dried encapsulates).

Encapsulation may be by any method known in the art, such as spray drying. Non-limiting typical encapsulates and methods of manufacture are described in PCT patent publication no. WO 2004/016234 that describes the use of shell microcapsules to encapsulate fragrance. Encapsulation technology is well known in the art and is generally directed to the encapsulation of core materials that require protection until time of use. The encapsulation of fragrances is also well known in the art. Fragrance microcapsules are often found in scratch and sniff inserts in magazines, in perfumes, deodorants, and a host of other applications. Antiperspirant/deodorant containing microcapsules are disclosed in U.S. Pat. No. 5,176,903. U.S. Pat. No. 5,876,755 discloses a composition comprising a substance encapsulated within a water-sensitive matrix so as to be releasable upon contact with water or aqueous solutions. Encapsulated fragrances have been added to fabric softeners and colognes (U.S. Pat. Nos. 4,446,032, 4,428,869, EP Pat. No. 1407753 and EP Pat. No. 1407753). Methods of manufacture of functional microcapsules are well known in the art, and are described in the aforementioned filings and in many others, eg U.S. Pat. Nos. 4,269,729, 4,102,806, GB Pat. No. 2073132, PCT patent publication nos. WO 2004/016234, WO 98/28396, WO 2003/55588, WO 2002/09663.

There are several types of microcapsules differentiated by their chemical nature, and by the encapsulating process. The choice of the type of microcapsules must be made according to the desired properties of the capsules in the contemplated applications.

The micro encapsulation principle is relatively simple. A thin polymer shell is created around droplets or particles of an active agent emulsified or dispersed in a carrier liquid. Highly preferred materials for the microcapsule shell wall are the aminoplast polymers comprising the reactive products of urea and aldehyde, e.g. formaldehyde. Such materials are those that are capable of acid condition polymerization from a water-soluble prepolymer state. Such prepolymers are made by reacting urea and formaldehyde in a formaldehyde:urea molar ratio of from about 1.2:1 to 2.6:1. Thiourea, cyanuramide, guanidine, N-alkyl ureas, phenols, sulfonamides, anilines and amines can be included in small amounts as modifiers for the urea. Polymers formed from such prepolymer materials under acid conditions are water-insoluble and can provide the requisite microcapsule friability characteristics. Microcapsules having the liquid cores and polymer shell walls as described above can be prepared by any conventional process which produces microcapsules of the requisite size, friability and water-insolubility. Generally, such methods as coacervation and interfacial polymerization can be employed in known manner to produce microcapsules of the desired characteristics. Such methods are described in U.S. Pat. Nos. 3,870,542; 3,415,758; and 3,041,288.

Microcapsules made from urea-formaldehyde shell materials can be made by a polycondensation process such as described in U.S. Pat. No. 3,516,941, incorporated herein by reference. By that process an aqueous solution of a urea-formaldehyde precondensate (methylol urea) is formed containing from about 3% to 30% by weight of the precondensate. Water-insoluble liquid core material (i.e., perfume) is dispersed throughout this solution in the form of microscopically-sized discrete droplets. While maintaining solution temperature between 20° C. and 90° C. acid is then added to catalyze polymerization of the dissolved urea-aldehyde performance. If the solution is rapidly agitated during this polymerization step, shells of water-insoluble urea-formaldehyde polymer form around the dispersed droplets and encapsulate the liquid core material.

Perfume ingredients for a perfume composition in accordance with the invention contain one or two phenyl groups, optionally substituted, and fall into five groups as set out above, wherein $R_1$ and $R_2$ are hydrocarbyl residues whose alkyl portions, when present, may be straight-chained or branched. $R_1$ and $R_2$ may also be linked as part of a ring structure. Non-limiting examples of perfume ingredients in groups 1 to 5 are presented below in Table 1, where trademarked materials marked 'Q' are available from Quest International, 'G' from Givaudan SA, and 'IFF' from International Flavors and Fragrances Inc. Where it is possible to allocate a material to two groups (or more) it should be allocated to the lower or lowest number category possible. This is exemplified by allyl phenoxyacetate which has ester as well as ether functionality, and is allocated to group 1 (ethers).

TABLE 1

Examples of Ingredients for use in perfumes of the invention

| COMMON NAME/TRADENAME* Molecular Formula | Chem Group | VP Class** | MOL. Wt. |
|---|---|---|---|
| ACETOPHENONE $C_8H_8O$ | 5 | III | 120 |
| ALLYL PHENOXYACETATE $C_{11}H_{12}O_3$ | 1 | I | 192 |
| AMYL SALICYLATE $C_{12}H_{16}O_3$ | 3 | I | 208 |
| ANETHOLE $C_{10}H_{12}O$ | 1 | II | 148 |
| ANISIC ALDEHYDE $C_8H_8O_2$ | 1 | II | 136 |
| ANTHER ™ (Q) (2-PHENYLETHYL ISOAMYL ETHER) $C_{13}H_{20}O$ | 1 | II | 192 |
| AQUANAL ™ (Q) (2-METHYL-3-(3,4-METHYLENE-DIOXYPHENYL)PROPANAL) $C_{11}H_{12}O_3$ | 1 | I | 192 |
| BENZYL ACETATE $C_9H_{10}O_2$ | 3 | III | 150 |
| BENZYL ACETONE $C_{10}H_{12}O_2$ | 5 | II | 148 |
| BENZYL TIGLATE (PHENYLMETHYL (2E)-2-METHYLBUT-2-ENOATE) $C_{12}H_{14}O_2$ | 3 | I | 190 |
| BOURGEONAL ™ (Q) (3-(4-TERT.BUTYLPHENYL)PROPANAL) $C_{13}H_{18}O$ | 2 | I | 190 |
| CANTHOXAL ™ (Q) (2-METHYL-3-(4-METHOXYPHENYL)PROPANAL) $C_{11}H_{14}O_2$ | 1 | I | 178 |
| CINNAMIC ALCOHOL $C_9H_{10}O$ | 4 | I | 134 |
| CYCLAMEN ALDEHYDE (2-METHYL-3-(4'-ISO-PROPYLPHENYL)PROPANAL) $C_{13}H_{18}O$ | 2 | I | 190 |
| DIPHENYL OXIDE $C_{12}H_{10}O$ | 1 | I | 170 |
| EFETAAL ™ (Q) ((2-{[1-(ETHYLOXY)ETHYL]OXY}ETHYL)BENZENE) $C_{12}H_{18}O_2$ | 1 | II | 194 |
| ETHYL BENZOATE $C_9H_{10}O_2$ | 3 | III | 150 |
| EUGENOL $C_{10}H_{12}O_2$ | 1 | I | 164 |
| FLORALOZONE ™ (IFF) (2,2-DIMETHYL-3-(PARA-ETHYL PHENYL)PROPANAL) $C_{13}H_{18}O$ | 2 | I | 190 |
| FLORHYDRAL ™ (G) (3-[3-(1-METHYLETHYL)PHENYL]BUTANAL) $C_{13}H_{18}O$ | 2 | I | 190 |
| ISOAMYL SALICYLATE $C_{12}H_{16}O_3$ | 3 | I | 208 |
| ISOBUTYL SALICYLATE $C_{11}H_{24}O_3$ | 3 | I | 194 |
| ISOEUGENOL $C_{10}H_{12}O_2$ | 1 | II | 164 |
| MARENIL (4-TERT-BUTYLPHENYLACETONITRILE) $C_{10}H_{15}N$ | 2 | I | 173 |
| MEFRANAL ™ (Q) (3-METHYL-5-PHENYLPENTANAL) $C_{12}H_{16}O$ | 2 | I | 176 |
| MEFROSOL ™ (Q) (3-METHYL-5-PHENYLPENTANOL) $C_{12}H_{18}O$ | 4 | I | 178 |
| METHYL ANTHRANILATE $C_8H_9NO_2$ | 3 | I | 151 |
| METHYL BENZOATE $C_8H_8O_2$ | 3 | III | 136 |
| METHYL CHAVICOL (4-METHOXY-1-(2-PROPENYL)-BENZENE) $C_{10}H_{12}O$ | 1 | III | 148 |
| METHYL CINNAMATE $C_{10}H_{10}O_2$ | 3 | I | 162 |
| METHYL EUGENOL $C_{11}H_{14}O_2$ | 1 | I | 178 |

TABLE 1-continued

Examples of Ingredients for use in perfumes of the invention

| COMMON NAME/TRADENAME* Molecular Formula | Chem Group | VP Class** | MOL. Wt. |
|---|---|---|---|
| METHYL PHENYLACETATE $C_9H_{10}O_2$ | 3 | III | 150 |
| METHYL SALICYLATE $C_8H_8O_3$ | 3 | III | 152 |
| para-CRESYL METHYL ETHER $C_8H_{10}O$ | 1 | III | 122 |
| para-METHOXYACETOPHENONE $C_9H_{10}O_2$ | 1 | II | 150 |
| para-METHYLACETOPHENONE $C_9H_{10}O$ | 5 | III | 134 |
| PELARGENE ™ (Q) (2,4-DIMETHYL-6-PHENYLDIHYDROPYRAN) $C_{13}H_{16}O$ | 1 | I | 188 |
| PETIOLE ™ (Q) (2-PHENYLETHYL ISOPROPYL ETHER) $C_{11}H_{16}O$ | 1 | III | 164 |
| PHENOXYETHYL ISOBUTYRATE $C_{12}H_{16}O_3$ | 1 | I | 192 |
| 2-PHENYLETHYL METHYL ETHER $C_9H_{12}O$ | 1 | III | 136 |
| 3-PHENYLPROPYL ALCOHOL $C_9H_{12}O$ | 4 | I | 136 |
| PHENYLACETALDEHYDE DIMETHYL ACETAL $C_{10}H_{14}O_2$ | 1 | III | 166 |
| PHENYLETHYL ACETATE $C_{10}H_{12}O_2$ | 3 | II | 164 |
| PHENYLETHYL FORMATE $C_9H_{10}O_2$ | 3 | II | 150 |
| RHUBAFURAN ™ (Q) (2,4-DIMETHYL-4-PHENYLTERAHYDROFURAN) $C_{12}H_{16}O$ | 1 | II | 176 |
| STYRALLYL ACETATE $C_{10}H_{12}O_2$ | 3 | III | 164 |
| YARA YARA (2-METHOXYNAPHTHALENE) $C_{11}H_{10}O$ | 1 | I | 158 |

KEY
*Alternative name given in parentheses
**VP Class: vapour pressure class
I - vp greater than 3 micron Hg but less than 30 micron Hg at 25° C.
II - vp greater than 30 micron Hg but less than 100 micron at 25° C.
III - vp at least 100 micron Hg at 25° C.
NOTES
All ingredients of Table 1 have a logP of at least 1.5

For the purposes of the present invention, useful materials possess molecular structures incorporating between 8 and 13 carbon atoms, an octanol/water partition coefficient (P) of about 30 (ie a logP value of at least 1.5, using base-10 logarithms) and an SVP at 25° C. of at least 3 micron Hg. This combination of features represents a balance between perfume ingredient diffusivity and its retentivity on a surface.

SVP is closely related to the inherent evaporation tendency of ingredients, so that for example substantive perfume ingredients such as musks have SVPs of less than 1 micron Hg at 25° C., typically 0.1 micron Hg or less. Vapour pressure data are available in the literature (eg in The Formulation of Cosmetics, Fragrances and Flavors, L Appell, Micelle Press, 3rd edition 1994), or may be estimated by various commercial software packages (eg ACDLabs from Advanced Chemistry Developments Inc of Toronto, Ontario).

The materials of the invention will generally have a minimum molecular weight around 110 a.m.u. and a maximum weight of around 210 depending upon the functional groups present. Therefore, low molecular weight materials inter alia methanol, ethanol, methyl acetate, and ethyl acetate, which are known components of some fragrance accords, are excluded from the scope of the invention. However, the formulator may wish to deliver these lower molecular weight materials as carriers, astringents, diluents, balancers, or as other suitable adjunct materials. Also excluded are essential oils such as lavender, rosemary and bergamot. These are well known in the perfumery industry as complex mixtures arising from the extraction of natural products using such techniques as steam distillation, solvent extraction, supercritical extraction, and cold pressing. Many examples are described in "The Essential Oils" by Guenther, volumes 1 to VI, published by Van Nostrand (1948-1952).

Additionally, in the perfume art, some materials having no odour or very faint odour are used as diluents or extenders. EP 404470 discloses a method of evaluating odour intensity on the basis of comparison with a 10% w/w solution of benzyl acetate in dipropylene glycol. This benzyl acetate solution is assigned a value of 100. Ingredients that score less than 75 on such a scale may be designated as very low odour. Non-limiting examples of very low odour materials are benzyl salicylate, hexyl cinnamic aldehyde, dipropylene glycol, diethyl phthalate, triethyl citrate, isopropyl myristate, and benzyl benzoate, all of which score ca. 70 or less on the aforementioned benzyl acetate scale. These materials may be used, for example, for solubilizing or diluting some solid or viscous perfume ingredients, for example, to improve handling and/or formulating, or stabilizing volatile ingredients, by reducing their vapor pressure. These materials are not counted in the definition of perfume ingredients nor in the weight percentage of the perfume compositions of the present invention.

The octanol-water partition coefficient (P) of a material i.e. the ratio of a material's equilibrium concentration in octanol and water, is well known in the literature as a measure of hydrophobicity and water solubility (see Hansch and Leo, Chemical Reviews, 526 to 616, (1971), 71; Hansch, Quinlan and Lawrence, J. Organic Chemistry, 347 to 350 (1968), 33). High partition coefficient values are more conveniently given in the form of their logarithm to the base 10, log P. While log P values can be measured experimentally i.e. directly, and measured log P data is available for many perfumes, log P values are most conveniently calculated or approximately estimated using mathematical algorithms. There are several recognised calculation or estimation methods available commercially and/or described in the literature (see for example A Leo, Chem. Rev 93(4), 1281-1306, (1993), "Calculating log P oct from structures"). Generally these models correlate highly but may for specific materials produce log P values which differ in absolute terms (by up to 0.5 log units or even more). However, no one model is universally accepted as the most accurate across all compounds. This is particularly true for estimates on materials of high log P (say 4 or greater). In the present specification, log P values are obtained using the estimation software commercially available as 'Log P' from Toronto-based Advanced Chemistry Development Inc (ACD) which is well-known to the scientific community, and accepted as providing high-quality predictions of log P values. References to log P values thus mean values obtained using the ACD software.

A requirement for a logP value of at least 1.5 calls for materials that are somewhat hydrophobic, and no better than sparingly soluble in water.

Perfume compositions of the invention may be incorporated into consumer products directly or, preferably, in encapsulated form, e.g. using encapsulation methods known in the art as described in the references above.

In a further aspect, the invention thus provides a consumer product comprising a perfume composition in accordance with the invention.

The consumer product conveniently comprises from 0.001% to 10% by weight; preferably from 0.005% to 6% by weight; more preferably from 0.01% to 4% by weight of at least one perfume composition in accordance with the invention.

The compositions find application in a wide range of consumer products and include, for example, room fresheners or room deodorants; clothes deodorants applied by washing machine applications such as in detergents, powders, liquids, whiteners or fabric softeners; in bathroom accessories such as paper towels, bathroom tissues, sanitary napkins, towellets, disposable wash cloths, disposable diapers, and diaper pail deodorants; household cleansers such as disinfectants and toilet bowl cleaners; cosmetic products such as antiperspirant and underarm deodorants, general body deodorants, hair care products such as hair sprays, conditioners, rinses, dyes, permanent waves, depilatories and hair straighteners; shampoos; foot care products; colognes, after shaves and body lotions; soaps and synthetic detergents; odour control products used, for example, during manufacturing processes, such as in the textile finishing industry and the printing industry; effluent and/or odour control products used, for example, in processes involved in pulping, stock yard and meat processing, sewage treatment, or garbage disposal; agricultural and pet care products such as for domestic animal and pet care and hen house effluents; and products for use in large scale closed air systems such as auditoriums, and subways and transport systems.

Consumer products can take a variety of forms including powders, bars, sticks, tablets, mousses, gels, liquids, sprays, and also fabric conditioning sheets to be placed with fabrics in a tumble dryer.

Consumer products according to the present invention may be produced by the same processing steps as used for prior consumer products, with the perfume composition according to the present invention being substituted for previous, conventional fragrance compositions Some consumer products are meant to be used and then rinsed off. The performant perfume compositions of this invention are particularly desirable for such products that are intended to be rinsed off, since the performant perfume compositions deposit extremely efficiently.

Perfume compositions of this invention are extremely desirable for consumer products as they minimize the amount of material in contact with the target substrate while providing long lasting effects even when the substrate is contacted with water. These performant perfume compositions minimize the material wasted, while still providing the good aesthetics that the consumers value.

The performant perfume composition of this invention, particularly when encapsulated, is substantive in-use and is capable of delivering a long lasting fragrance impression in use and ensures a strong fragrance impression for consumers in the final application. In addition, an encapsulated performant perfume composition is protected against, for example, oxygen and moisture during storage and processing.

While it is known in the prior art to formulate substantive (enduring) perfumes and to encapsulate fragrance compositions, it has hitherto not been known that maximum performant effect can be achieved from encapsulated fragrance compositions through the use of non-substantive fragrance compositions and in particular through the use of fragrance compositions comprising non-substantive fragrance ingredients selected according to the teachings of this invention.

This invention can provide high perfume performance compositions, particularly when in encapsulated form, through the unexpected utility of non-substantive fragrance materials, with the compositions being effectively retained and remaining on target substrates to provide long lasting strongly diffusive fragrance benefits.

The performant perfume compositions of the invention can thus provide a combination of improved performance and substantivity.

EXAMPLES

The following Examples further describe and demonstrate the preferred embodiments within the scope of the present invention. The Examples are given solely for the purpose of illustration and are not to be construed as limitations of the present invention as many variations thereof are possible without departing from its scope. All percentages, ratios, and parts herein, are by weight and are approximations, unless otherwise stated.

Example 1

Performant Perfume Compositions

TABLE 2

Performant Perfumes PPA01 and PPA02

| INGREDIENT | Ingredient Group# | PPA01 w/w % | PPA02 w/w % |
|---|---|---|---|
| ANISIC ALDEHYDE | 1 | 7.6 | |
| ANTHER (Q) | 1 | | 3 |
| BENZALDEHYDE | 1 | 2.6 | |
| BENZYL ACETATE | 3 | 3 | 12 |
| BENZYL ACETONE | 5 | | 5 |
| BENZYL TIGLATE | 3 | | 2 |
| BOURGEONAL (Q) | 2 | 2.4 | |
| CINEOLE | n/a | | 1 |
| CINNAMON BARK OIL | n/a | 0.4 | |
| cis-3-HEXENYL SALICYLATE | n/a | | 2 |
| COUMARIN | n/a | 7.6 | |
| DAMASCONE, DELTA- | n/a | | 2 |
| DIMETHYL BENZYL CARBINYL ACETATE | n/a | 6.4 | |
| EUGENOL | 1 | 2.6 | 3 |
| GERANIUM OIL | n/a | 1.2 | |
| HELIOTROPIN | n/a | 5 | |
| INDOLE | n/a | | 0.5 |
| ISOBUTYL SALICYLATE | 3 | 3.8 | 4 |
| ISOEUGENOL | 1 | 1.2 | |
| JASMATONE (Q) | n/a | | 2 |
| LINALOL | n/a | | 15 |
| MEFRANAL (Q) | n/a | 1.2 | 1 |
| MEFROSOL (Q) | 4 | 10 | 10 |
| METHYL BENZOATE | 3 | 0.6 | 2 |
| METHYL CINNAMATE | 3 | 2.6 | |
| METHYL DIHYDROJASMONATE | n/a | | 12 |
| METHYL IONONE, ALPHA-ISO- | n/a | 4 | |
| METHYL PHENYLACETATE | 3 | 0.6 | |
| NOPYL ACETATE | n/a | 5 | |
| PARA METHOXY ACETOPHENONE | 1 | 4 | |
| PARA METHYL ACETOPHENONE | 5 | 0.6 | |
| PARA-CRESYL METHYL ETHER | 1 | | 2 |
| PATCHOULI ACID WASHED | n/a | 2 | |
| PELARGENE (Q) | 1 | 0.6 | |
| PHENOXYETHYL ISOBUTYRATE, BETA- | 1 | 10 | |
| PHENYLETHYL ACETATE | 3 | 4 | 12 |
| PHENYLPROPYL ALCOHOL | 4 | 3 | |
| PRENYL ACETATE | n/a | | 2 |
| RASPBERRY KETONE* | n/a | | 0.5 |
| YARA YARA** | 1 | 4 | 4 |
| YLANG EXTRA | | 4 | 3 |
| totals | | 100% | 100% |

Group Summaries

| | PPA01 w/w % | PPA02 w/w % |
|---|---|---|
| Group 1 | 32.6 | 12 |
| Group 2 | 2.4 | 0 |
| Group 3 | 14.6 | 32 |
| Group 4 | 13 | 10 |
| Group 5 | 0.6 | 5 |
| Total Groups 1-5 | 63.2 | 59 |

KEY
*4-(p-HYDROXYPHENYL)BUTAN-2-ONE
**2-METHOXYNAPHTHALENE
See Table 1; n/a = not within groups 1 to 5.
Suppliers
F—Firmenich
Q—Quest International Table 2 shows the compositions of two performant perfumes and identifies which ingredients conform to the requirements of the invention. An analysis of the amounts of perfume ingredients in groups 1 to 5 is shown at the bottom of the table. Trademarks are as above.

Example 2

Encapsulated samples of perfumes PPA01 and PPA02 were prepared according to example 14 of WO 2004/016234 to produce Encapsulates PPA201 and PPA202. Reference Encapsulate A was also prepared by the same method using Perfume A (HW4180B, available from Quest International) disclosed in the same PCT Application. Perfume A contained less than 10% of ingredients from classes 1 to 5, and approximately 20% of aromatic ingredients (ie those possessing a phenyl or aryl group) not conforming to one or more of the criteria for vapour pressure, molecular structure and logP.

These encapsulates were then incorporated into Rinse Conditioner Base C (disclosed in WO 2004/016234) at an equivalent perfume level of 0.2% and a standard wash trial carried out for each of the samples (two perfumes of this invention and Perfume A). Terry towelling monitor cloths were then removed from each wash load and dried by static line drying. The perfume intensity present on each cloth was then evaluated by a panel of three expert evaluators. In each case, the perfume intensity was significantly higher for samples containing the perfumes PPA01 and PPA02 of this invention, compared to reference Perfume A, thus illustrating the utility of the invention compared to a prior art perfume.

The invention claimed is:

1. A perfume composition comprising over 60% by weight of perfume ingredients that are characterized by (i) a molecular formula possessing from 8 to 13 carbon atoms, including at least one phenyl moiety, substituted or unsubstituted; (ii) an octanol/water partition coefficient expressed as a log to the base 10 (log P) of at least 1.5; (iii) a saturated vapour pressure (SVP) of at least 3 micron Hg at 25° C.; and (iv) membership of one of the following groups:

1. ethers of general formula $R_1OR_2$;
2. aldehydes or nitriles of general formula $R_1X$, wherein X is CHO (formyl group) or ON (cyano group);
3. esters of general formula $R_1CO_2R_2$;
4. alcohols or phenols of general formula $R_1OH$; or
5. ketones of general formula $R_1COR_2$ wherein $R_1$ and $R_2$ are alkyl, aryl, aralkyl or alkaryl residues, optionally substituted, whose alkyl moieties may be straight-chained or branched, and which may be linked as part of a ring structure;

provided that (a) the perfume ingredients do not include essential oils or components thereof; (b) where a perfume ingredient could be assigned to more than one of the above groups, said ingredient is allocated to the group having the lower or lowest number; (c) any components used as non-odorous or very low odour diluents, solvents or vehicles of the perfume composition are not included in the calculation of the percentage composition; and (d) at least three of the groups (1) to (5) must each comprise perfume ingredients amounting to at least 5% by weight of the perfume composition.

2. A perfume composition according to claim 1, wherein the perfume ingredients constitute at least 80% by weight of the perfume composition.

3. A perfume composition according to claim 1 or 2, wherein at least one of the perfume ingredients has an SVP of at least 30 micron Hg at 25° C.

4. A perfume composition according to claim 3, wherein the perfume ingredients include materials selected from the group consisting of: 2,2-dimethyl-3-(para-ethylphenyl)propanal, 2,4-dimethyl-4-phenyltetrahydrofuran, 2,4-dimethyl-6-phenyldihydropyran, 2-{[1-(ethyloxy)ethyl]oxy}ethyl) benzene, 2-methoxynaphthalene, 2-methyl-3-(3,4-methylene-dioxyphenyl)propanal, 2-methyl-3-(4'-isopropylphenyl)propanal, 2-methyl-3-(4-methoxyphenyl) propanal, 2-phenylethyl isoamyl ether, 2-phenylethyl isopropyl ether, 2-phenylethyl methyl ether, 3-(4-tert.butylphenyl)propanal, 3-[3-(1-methylethyl)phenyl]butanal, 3-methyl-5-phenylpentanal, 3-methyl-5-phenylpentanol, 3-phenylpropyl alcohol, 4-methoxy-1-(2-propenyl)-benzene, 4-tert-butylphenylacetonitrile, acetophenone, allyl phenoxyacetate, amyl salicylate, anethole, anisic aldehyde, benzyl acetate, benzyl acetone, cinnamic alcohol, diphenyl oxide, ethyl benzoate, eugenol, isoamyl salicylate, isobutyl salicylate, isoeugenol, methyl anthranilate, methyl benzoate, methyl cinnamate, methyl eugenol, methyl phenylacetate, methyl salicylate, para-cresyl methyl ether, para-methoxyacetophenone, para-methylacetophenone, phenoxyethyl isobutyrate, phenylacetaldehyde dimethyl acetal, phenylethyl acetate, phenylethyl formate, phenylmethyl (2E)-2-methylbut-2-enoate, styrallyl acetate.

5. A perfume composition according to claim 1, including perfume ingredients falling in all five of the groups.

6. A perfume composition according to claim 1, wherein at least three groups include perfume ingredients amounting to at least 10% of the weight of the perfume composition.

7. A perfume composition according to claim 1, wherein at least one group includes at least two different perfume ingredients.

8. A perfume composition according to claim 7, wherein at least two groups include at least three different perfume ingredients.

9. A perfume composition according to claim 1, wherein the perfume composition is encapsulated.

10. A consumer product comprising a perfume composition according to claim 1.

11. A consumer product according to claim 10, comprising from 0.001% to 10% by weight of perfume composition.

* * * * *